United States Patent [19]

Kolbach

[11] E Re. 29,789

[45] Reissued Oct. 3, 1978

[54] ABSORBENT ARTICLES FOR DISPOSABLE DIAPER

[75] Inventor: Charles G. Kolbach, Media, Pa.

[73] Assignee: Scott Paper Company, Philadelphia, Pa.

[21] Appl. No.: 634,826

[22] Filed: Nov. 20, 1975

Related U.S. Patent Documents

Reissue of:

[64] Patent No.: 3,860,002
Issued: Jan. 14, 1975
Appl. No.: 360,124
Filed: May 14, 1973

[51] Int. Cl.[2] ..... A61F 13/16

[52] U.S. Cl. ..... 128/284; 428/195; 428/290; 128/287

[58] Field of Search ..... 128/284, 287

[56] References Cited

U.S. PATENT DOCUMENTS

| | | | |
|---|---|---|---|
| 2,788,003 | 4/1957 | Morin | 128/287 |
| 3,386,442 | 6/1968 | Sabee | 128/287 |
| 3,430,629 | 3/1969 | Murphy | 128/284 |
| 3,444,859 | 5/1969 | Kalwaites | 128/284 |
| 3,612,055 | 10/1973 | Mesek et al. | 128/287 |
| 3,766,922 | 10/1973 | Krusko | 128/284 |
| 3,828,783 | 8/1974 | Kennette | 128/284 |
| 3,848,598 | 11/1974 | Mesek | 128/287 |

*Primary Examiner*—Robert W. Michell
*Assistant Examiner*—J. Stremcha
*Attorney, Agent, or Firm*—Martin L. Faigus; William J. Foley

[57] ABSTRACT

An absorbent article includes an air-laid fibrous web having a medial portion of a greater basis weight than flanking end and side portions. The fibers forming one surface of the web are adhesively bonded together to provide an abrasion resistant, non-pilling, facing layer, and also to aid in maintaining the structural integrity of the web. The fibers forming the other surface of the web are either adhesively bonded together, or a separate backing sheet, preferably in the form of a waterproof plastic sheet, is adhered directly to the other surface of the web to form a stabilized backing layer. The above constructions are adapted for use as disposable diapers.

Apparatus of this invention includes a vacuum box having an open end underlying a discrete section of a foraminous forming surface so that regions of the forming surface extend beyond the open end of the vacuum box. Vacuum connection means permit the establishment of a different pressure drop across the discrete section of the foraminous forming surface overlying the open end of the vacuum box than through regions of the foraminous forming surface extending beyond the vacuum box. Drive means move the foraminous forming surface and vacuum box in registration with each other through a web forming area for maintaining the same discrete section of the foraminous forming surface in overlying relationship with the open end of the vacuum box as the foraminous forming surface and the vacuum box are moved through the web forming area.

The method of this invention employs the above-described apparatus in which the foraminous forming surface extends beyond, and completely circumscribes the open end of the vacuum box. A greater pressure drop is established through the discrete section of the foraminous forming surface overlying the vacuum box than through the regions extending beyond the vacuum box to form a fibrous web having a medial portion with a greater basis weight of fibers therein than in flanking end and side portions of the web.

22 Claims, 19 Drawing Figures

ABSORBENT ARTICLES FOR DISPOSABLE DIAPER

Matter enclosed in heavy brackets [ ] appears in the original patent but forms no part of this reissue specification; matter printed in italics indicates the additions made by reissue.

*RELATED APPLICATIONS*

*This is an application for reissue of U.S. Pat. No. 3,860,002, granted on Jan. 14, 1975 on an application for ABSORBENT ARTICLES, Ser. No. 360,124, filed May 14, 1973.*

BACKGROUND OF THE INVENTION

1. Field of the Invention

This invention relates to air-laid fibrous webs, and to methods and apparatus for manufacturing same.

2. Description of the Prior Art

Absorbent fibrous members having a thick center region therein have been utilized in sanitary products, such as disposable diapers, as exemplified in U.S. Pat. No. 2,890,700, issued to LonbergHolm; U.S. Pat. No. 3,430,629, issued to Murphy; U.S. Pat. No. 3,509,604, issued to Furbeck; U.S. Pat. No. 3,598,680, issued to Lee; and U.S. Pat. No. 3,682,761, issued to Lee et al. The absorbent members described in all of the above patents are internal components of a sanitary product. Such absorbent members normally are not sufficiently self-sustaining to be utilized alone, or in conjunction with only a backing layer, to form a complete sanitary product, such as a disposable diaper. Stating this another way, separate facing and backing sheets normally are required to provide structural support for such absorbent members. Therefore, the sanitary product constructions disclosed in the above patents must be fabricated by utilizing fairly complicated converting equipment in which the absorbent member is sandwiched between opposed facing and backing sheets, and in which the facing and backing sheets are adhered together. In addition, one or both of the facing and backing sheets is usually an adhesively bonded web to begin with. Therefore, adhesive is not only utilized to form a self-sustaining facing and/or backing web, but additional adhesive is required to adhere the facing and backing webs to each other. It is highly desirable to decrease the amount of adhesive necessary to fabricate sanitary products to thereby reduce their cost of manufacture. Reduced cost is an important consideration in products such as disposble diapers which are intended for disposal after a single use.

The absorbent internal members disclosed in the patents to Murphy (U.S. Pat. No. 3,430,629), Furbeck (U.S. Pat. No. 3,509,604), Lee (U.S. Pat. No. 3,598,680), and Lee et al (U.S. Pat. No. 3,682,761), all have a thick central region which extends the full length of the absorbent member, and thinner flanking side portions. This construction provides a conformable, snug fit in the thigh region of a wearer while providing a thicker, more absorbent section in the perineal region where it is needed to retain body fluids. However, the forward and rearward regions of the absorbent members include a portion of the thick central region as well as a portion of the thinner flanking side portions. Diapers having a forward and rearward region with thickness variations along the transverse extent thereof do not provide as comformable a waste band region as a diaper in which the forward and rearward regions have a substantially uniform thickness extending for the full transverse extent thereof.

The absorbent member employed in the diaper disclosed in Lonberg-Holm includes a heavier basis weight medial portion than flanking end and side portions thereof. This absorbent member is formed from a plurality of plies of crepe paper wadding which must be properly positioned relative to each other on suitable converting equipment. Lonberg-Holm discloses that the layers or plies could include a mass of fibrous material which is uniform in character and of a varying thickness such that there are no physically distinct layers. However, this discussion implies the separate formation of fibrous members which are married together to achieve sufficient interlocking between fibers to render the layers physically indistinct. Such a method of forming an absorbent member still requires suitable equipment for precisely aligning various fibrous webs together in order to achieve the varying thickness construction. In addition, as stated above, Lonberg-Holm is not directed to an absorbent member which can be utilized either by itself as a sanitary product, or in conjunction with only a backing layer. Lonberg-Holm requires an absorbent member which is structurally held in place by being disposed between separate facing and backing layers in the conventional manner employed today in disposable diapers.

Prior art apparatus and method for forming air-laid, profiled fibrous webs have included means for establishing a non-uniform basis weight distribution in the cross-machine direction of web formation. However, such apparatus do not include means for affecting a non-uniform basis weight distribution in the machine direction of web formation by initially depositing different weights of fibers in different areas. For example, the Lee et al. apparatus (U.S. Pat. No. 3,682,761) includes a plurality of stationary vacuum chambers disposed behind a moving foraminous surface upon which an air-lay fibrous web is formed. Therefore, any transverse section of the forming surface passes over the same bank of vacuum boxes, and accordingly, the machine direction basis weight of the fibrous web formed in any transverse region of the forming surface will be sustanially the same. However, by properly adjusting the vacuum levels in the various banks of vacuum boxes, a crossmachine direction basis weight variation can be achieved.

In the Lee and Furbeck apparatus separate continuous airlaid webs are formed, and are deposited in partial overlapping relationship with each other to provide a centrally disposed region having a greater basis weight than flanking side portions. This arragement for forming a profiled fibrous web also results in the formation of a thickened region extending for the full length of the absorbent air-laid web.

SUMMARY OF THE INVENTION

Absorbent articles of this invention include a fibrous web in the form of a unitary assemblage of randomly arranged fibers. The webs include a medial portion integrally joined through said randomly arranged fibers to flanking side portions and flanking end portions; said medial portio having a greater basis weight and thickness than said flanking side and end portions. Preferably, the flanking side and end portions in each fibrous web have substantially the same average thickness and basis weight. All embodiments include an abrasion resistant, non-pilling, facing layer provided by an adhesive distribution which bonds together the fibers forming one surface of the fibrous webs. The adhesive distribution also functions to establish structural integrity of the webs. If such webs are intended for use by themselves (i.e., without the use of a separate plastic, or other backing sheet) as a disposable diaper, such fibrous webs are provided with a stabilized backing layer by an adhesive distribution which bonds together the fibers forming the back surfaces of the webs. A stabilized backing layer is provided in all embodiments, either by adhesive or a separate sheet.

The adhesive distribution within the fibrous webs can be varied; however, in all embodiments the adhesive distribution must form an abrasion resistant, non-pilling, facing layer. Also, the adhesive distribution must provide a structurally stable backing layer when the fibrous webs are to be utilized by themselves (i.e., with no separate backing sheet) as a unitary sanitary product. The specific thickness and basis weight of the various portions of the fibrous webs is dictated by the specific use to which the absorbent articles are to be put. For example, when an absorbent article is intended for use as a disposable diaper, the thickness and basis weight of the various portions of the fibrous web will be dictated by the specific use to which the diaper is to be put, i.e., daytime, nighttime, toddler, infant, etc.

The fibrous webs utilized in this invention can be provided with an embossed pattern in the thick medial portion and/or the flanking side and end portions. Alternatively, the webs can be completely free of any embossed pattern; however, embossed patterns are desired for some applications to aid in wicking body fluids which are impinged on the fibrous webs to provide effective utilization of the absorptive material.

The higher basis weight medial portion of the fibrous webs can be of a substantially uniform basis weight, or can be profiled to provide the greatest basis weight in certain sections thereof. For example, when a fibrous web is intended for use as a disposable diaper for a girl, the center section of the medial portion can be provided with a greater basis weight of fibers therein than flanking end sections thereof. Alternatively, when a fibrous web is intended for use as a disposable diaper for a boy, a forward section of the medial portion can be provied with a greater basis weight of fibers therein than a rearward section thereof.

The specific shape of the high basis weight medial portion of the fibrous web can be varied within wide limits. For example, the thick medial portion can be substantially rectangular, or alternatively, can be contoured to include a reduced width crotch region which provides a more comformable structure in the perineal region of a wearer.

In a preferred use, the absorbent articles of this invention are employed as disposable diapers. The disposable diapers are placed on a wearer with the abrasion resistant, non-pilling, facing layer of the fibrous web in contacting relationship with the wearer. The high basis weight medial portion of the web is disposed in the perineal region of the wearer to provide a highly absorptive area for retaining body fluids. Although the medial portion is fairly thick, the construction is comfortable and conformable because the medial portion does not extend for the full length or width of the web. In the most preferred embodiment of this invention the fibrous web includes a contoured medial portion having a reduced width crotch region to enhance conformability of the diaper. The low basis weight flanking side portions provide an extremely conformable region which snugly engages the thigh region of the wearer to prevent leakage of body fluids from the diaper. The low basis weight flanking end portions of the diaper provides a conformable waist band region for closely and uniformly engaging the front and back regions of a wearer. The most desirable fit is achieved in the preferred construction in which the flanking end and side portions are of substantially the same average thickness and basis weight.

Both the apparatus and method of this invention for forming fibrous webs employ a foraminous forming surface and at least one vacuum box underlying a discrete section of the forming surface. Vacuum connection means are provided for permitting the establishment of a pressure drop across the discrete section of the foraminous forming surface overlying the vacuum box that is different from a pressure drop which can be estalished through the regions of the foraminous forming surface extending beyond peripheral walls of the vacuum box. The foraminous forming surface and the vacuum box are moved in registration with each other through a web forming area so that the same region of the foraminous forming surface is always in overlying relationship with the vacuum box. Therefore, the apparatus of this invention permits the weight of fibers deposited in the region of the foraminous forming surface overlying the vacuum box to be controlled independently of the weight of fibers deposited in the regions of the foraminous forming surface which extend beyond peripheral walls of said vacuum box.

In the preferred method of this invention in which the medial portion of the fibrous web is provided with a greater basis weight of fibers therein than flanking end and side portions thereof, the foraminous forming surface extends beyond all peripheral walls of the vacuum box. A greater pressure drop is established through the vacuum box, and accordingly, through the discrete section of the foraminous forming surface overlying the vacuum box, than through regions of the foraminous forming surface extending beyond peripheral walls of the vacuum box.

In the most preferred method and apparatus of this invention the foraminous forming surface overlying the vacuum box is a button wall of a three-dimensional compartment in which the thickened medial region is formed. The specific shape of the thickened medial region is dictated by the shape of the three-dimensional compartment. The peripheral walls of the vacuum box define an opening which has substantially the same shape as the three-dimensional compartment.

To the best of applicant's knowledge, no prior art airlay apparatus employs a foraminous forming surface and at least one vacuum box which are moved in registration with each other through a web forming area as described above. Accordingly, applicant's method and apparatus permits precise separate control of the basis weight of fibers deposited in discrete sections of the fibrous web to achieve formation of the fibrous webs employed in this invention.

Other objects and advantages of this invention will be better understood by referring to the detailed description which follows, taken in conjunction with the drawings.

DESCRIPTION OF THE PREFERRED EMBODIMENTS OF THIS INVENTION

Figure 1:
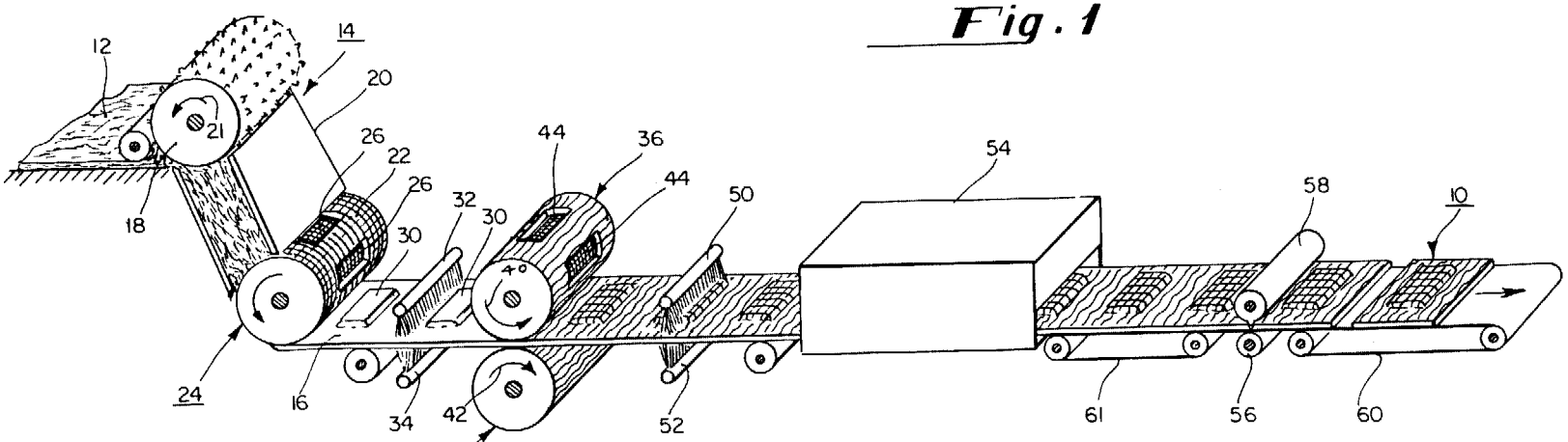
FIG. 1 is a schematic isometric view showing the sequential steps in forming unitary fibrous webs according to a preferred method of this invention.

Referring to FIG. 1, a preferred process of this invention will be described for forming absorbent articles 10. A fibrous feed mat 12 is directed into an air-lay web forming device 14 for forming a continuous fibrous web 16. The web forming device 14 includes a fiberizing roll 18 which is rotatably driven in the direction indicated by arrow 21 to separate fibers from the mat 12, and to entrain the fibers in air to form an air suspension of fibers within a formation duct 20. The air suspension of fibers is directed toward a foraminous forming surface 22 of a condenser roll assembly 24. The air of the suspension is directed through the foraminous forming surface 22, and the fibers in the suspension are condensed on the forming surface in the form of a continuous fibrous web 16. The foraminous forming surface 22 includes cirumferentially spaced, three-dimensional compartments 26. A greater weight of fibers is directed into the three-dimensional compartments 26 then onto surrounding regions of the foraminous forming surface 22 to form the continuous fibrous web 16 with spaced regions 30 having a greater weight of fibers per unit area (i.e., basis weight) than circumscribing regions of said web. The construction of the condenser roll assembly 24 and its mode of operation for forming a fibrous web with thickened regions 30 forms an important aspect of the present invention, and will be described in detail latter in this application.

The fibrous feed mat 12 can include a major proportion by weight of short cellulosic fibers of a papermaking length less than ¼ inch, and a minor proportion by weight of reinforcing fibers over ¼ inch in length. Preferably the shot cellulosic fiers are wood pulp fibers since they are highly absorbent, readily available and inexpensive. Other short cellulosic fibers such as cotton linters, can also be utilized. The reinforcing fibers preferably are of a staple length between about ½ inch and 3 inches in length, and these fibers are well known in the prior art. In a preferred embodiment of this invention the fibrous feed mat 12 includes from between about 75 percent to about 90 percent by weight wood pulp fibers, and from about 10 percent to about 25 percent by weight rayon fibers, 1½ length, 3 denier. It is also within the scope of this invention to employ a fibrous feed mat 12 of 100 percent short cellulosic fibers of a papermaking length less than ¼ inch; however, the inclusion of longer fibers is preferred to reinforce the structure.

The continuous fibrous web 16 is directed past an upper water spray unit 32 and lower water spray unit 34 for adjusting the moisture level in the web so that it will receive and retain an embossed pattern impressed therein. Preferably, the moisture level in the web is adjusted to from between about 6 percent and about 35 percent by weight, based on the bone dry weight of the fibrous web 16.

Figure 4:
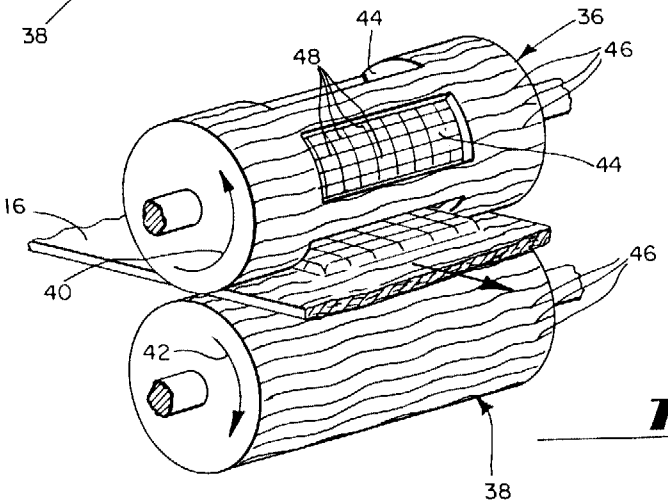
FIG. 4 is an isometric view of embossing rolls utilized according to one preferred method of this invention.

Referring to FIGS. 1 and 4, after the fibrous web 16 has passed the water spray units, it is directed through a nip defined between an upper embossing roll 36 and a lower embossing roll 38 which are positively driven in the direction indicated by arrows 40 and 42, respectively, by any suitable drive means (not shown). The upper embossing roll 36 has a plurality of circumferentially spaced recesses 44 therein, and is driven in synchronism with the feed of the fibrous web 16 so that the recesses 40 align with the thickened regions 30 of said fibrous web. The upper and lower embossing rolls have raised projections 46 disposed in a wavy line pattern in their outermost surfaces. The boddom wall of each of the recesses 40 includes raised surfaces 48 disposed in a different pattern than the raised surfaces 46. Specifically, the raised surfaces 48 shown in FIGS. 1 and 4 include a plurality of axial extending raised projections crossing a plurality of circumferentially directed raised projections to form a waffle-like pattern.

The specific pattern of raised projections in the embossing rolls 36 and 38, as described in the preceeding paragraph, is illustrative of particular embossing patterns which can be utilized; however, the specific pattern of projections is not critical in the present invention. The purpose of including embossed regions in the fibrous web 16 is to aid in directing fluid impinged on the web along substantially the entire extent of said web to provide effective utilization of its absorbing capacity. Any embossed pattern can be utilized which achieves this objective, and in some applications, one or both of the embossed patterns can be omitted. For example, this invention also relates to absorbent articles employing fibrous webs which are completely unembossed, as well as to absorbent articles employing fibrous webs in which only the spaced, thickened regions 30 are embossed. The embossing rolls 36 and 38 will be appropriately modified to establish the desired embossed pattern in the fibrous web 16.

Referring to FIG. 1, after the fibrous web 16 has passed through the nip of the embossing rolls 36 and 38, it is directed through an adhesive station, which is illustrated in FIG. 1 as including an upper adhesive spray unit 50 and a lower adhesive spray unit 52. The adhesive is applied to bond substantially all of the surface fibers together to provide a self-sustaining web with abrasion resistant, non-pilling surfaces. Any suitable adhesive normally employed in the manufacture of air-laid absorbent products can be utilized. The preferred binders are of the self-curing acrylic latex family, the urethane family, or other binders which can be utilized in low viscosity solutions or suspensions. If desired, the adhesive applied to the lower surface of the fibrous web 16 can include a water repellent agent therein to provide a fluid impervious backing layer, and the adhesive applied to the upper surface can include a wetting agent to enhance fluid absorbency into the interior regions of said web.

The method of applying adhesive to the fibrous web can be varied. For example, the adhesive can be flowed onto the fibrous web 16 from a weir box in excessive quantities, and a major proportion of the adhesive can be withdrawn by the application of suction from below the fabric, according to the method set forth in U.S. Pat. No. 3,663,348, issued to Liloia et al, and assigned to Johnson & Johnson.

When the absorbent article includes a fluid impervious backing sheet, the application of adhesive to the lower surface of the fibrous web 16 web can be omitted entirely, and the adhesive can be applied to the separate backing sheet prior to adhering the backing sheet to the fibrous web. Alternatively, the backing sheet can be adhered to the fibrous web by directly extruding the backing sheet onto the lower surface of said fibrous web in the manner suggested in U.S. Pat. No. 3,402,715, issued to Liloia et al, and assigned to Johnson & Johnson.

After adhesive has been applied to the fibrous web 16, said web is directed through an oven 54 to dry the fibrous web and cure or set the adhesive. After the adhesive has been set the fibrous web 16 is directed to a cutting staton which includes a lower anvil roll 56 and an upper cutter roll 58. The continuous fibrous web 16 is separated into discrete, absorbent, air-laid absorbent articles 10 at the cutting station, and these discrete articles 10 can be spaced from each other by a take-off conveyor 60 which is moving at a faster speed than upstream conveyors (only one of which is shown at 61) which direct the continuous fibrous web 16 through the process. The spaced articles 10 can be directed to further processing stations (not shown), e.g. turning, folding and packaging stations.

Figure 10:
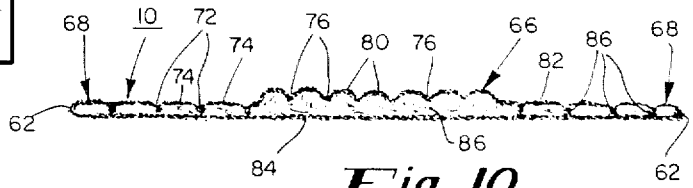
FIG. 10 is a sectional view along line 10—10 of FIG. 9.
Figure 9:
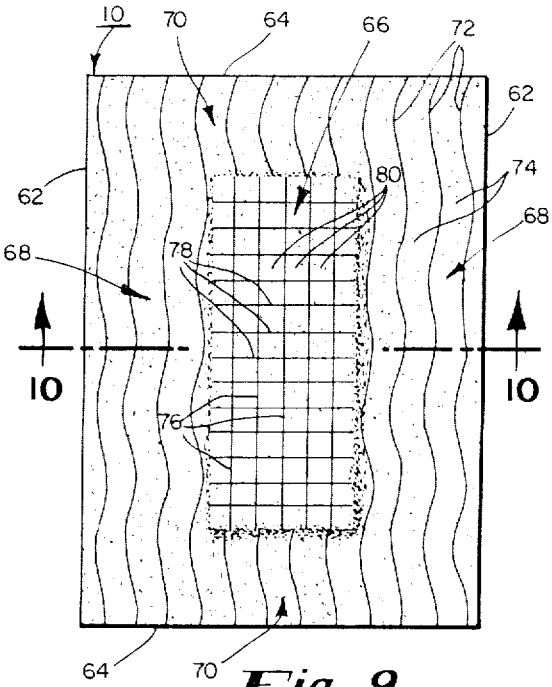

Referring to FIGS. 9 and 10, details of the absorbent article 10 are shown. This absorbent article 10 is intended for use as a disposable diaper and has a transverse dimension defined between spaced elongate side edges 62, and an elongate dimension defined between spaced end edges 64. The absorbent article 10 includes a medial portion 66 integrally joined through randomly arranged fibers to flanking side portions 68 and flanking end portion 70; said medial portion having a greater basis weight and thickness than said flanking side and end portions. Preferably, the flanking side portions 68 and flanking end portions 70 are of substantially the same, uniform, thickness and basis weight.

The flanking side portions 68 and end portions 70 include an embossed pattern therein in the form of continuous, compressed channels 72 having a wavy-line configuration. These compressed channels are spaced from each other by relatively uncompressed high loft regions 74. The medial portion 66 includes an embossed pattern in the form of transversely spaced, longitudinally extending channels 76 and longitudinally spaced, transversely extending channels 78 to define a waffle-like pattern. High loft, substantially uncompressed regions 76 and the transverse channels 78.

Referring specifically to FIG. 10, an upper adhesive layer bonds substantially all of the surface fibers together to provide an abrasion resistant, non-pilling facing surface 82 which can be positioned in contact with a wearer without fiber pilling or dusting. The upper adhesive layer penetrates only partially through the thickness of the web in the thick medial portions 66 thereof, and in the high loft regions 74 of the flanking side portions 68 and flanking end portions 70. A lower adhesive layer bonds substantially all of the lower surface fibers together to provide an abrasion-resistant, non-pilling back surface 84. This lower adhesive layer penetrates only partially through the thickness of the web in the medial portion thereof and in the high loft regions 74 of the flanking side portions 68 and the flanking end portions 70. The upper adhesive layer and lower adhesive layer cooperate to define adhesive networks 86 extending completely through the web in the compressed channel regions 72 of the flanking side portions 68 and end portions 70. An interior region 87 disposed between the upper and lower adhesive layers in the medial portion 66 is substantially free of adhesive, and therefore provides an excellent moisture absorbent area for retaining body fluids directed onto the medial portion 66 of the absorbent article 10. The bonded networks 86 which penetrate completely through the web in the flanking side and end portions thereof enhance the tensile strength of the web and provide a substantially non-pealing construction. The interior portions of the web in the high loft regions 74 of the flanking side and end portions ae substantially free of adhesive to provide regions of good fluid containing capacity.

In use, the diaper 10 is placed on a wearer with the thick, medial portion 66 disposed in the perineal region. Urine is initially directed onto the medial portion 66 and is wicked both longitudinally and transversely by virture of the high capillary forces in the longitudinal channels 76 and transverse channels 78. Any body fluids which are directed into the flanking side and end portions of the diaper will be wicked substantially in the longitudinal direction of the web 10 by the compressed channels 72. The greatest tendancy for leakage occurs at the longitudinal side edges 62, and the longitudinally extending channels 72 function to wick the body fluids longitudinally to thereby impede transverse flow toward said side edges.

The flanking side portion 68 and end portions 70 have substantially the same basis weight. The specifc basis weight utilized is dictated by the particular use of the diaper, i.e., infant, toddler, overnight, daytime, etc. However, in the most preferred embodiment of this invention the basis weight of the flanking side portions 68 and end portions 70 is in the range of from about 1.5 ounces per square yard to about 6 ounces per square yard. Preferably, the density of the flanking side portions 68 and end portions 70 is in the range of from about 0.05 grams per cubic centimeter to about 0.15 grams per cubic centimeter. (Determined in accordance with ASTM Method D-1777, set forth in the manual of the American Society for Testing materials).

The medial portion 66 may be slightly conpressed; having a slightly higher density than the flanking side portions 68 and end portions 70. Preferably, the density of the medial portion 66 will be in the range of from about 0.1 gram per cubic centimeter to about 0.2 grams per cubic centimeter. The basis weight of the medial portin 66 can be varied depending upon the required absorptive capacity, and the required absorptive capacity will vary depending upon the particular use of the diaper, i.e., infant, toddler, overnight, daytime, etc. Generally, the basis weight of the medial portion 66 will be in the range of from between about 8 ounces per square yard to about 50 ounces per square yard. Also the specific dimensions of the diaper, including the dimensions of the memdial portion 66, can be varied depending upon the intended use of the diaper.

As explained earlier in this application the specific adhesive distribution in the absorbent article 10 can be varied within wide limits. However, it is critical to this invention that the adhesive bond the fibers together in the upper surface thereof to provide an abrasion resistant, non-pilling facing surface 82 which can be positioned in contact with a wearer without piling, or dusting during use. Moreover, if the absorbent article 10 is intended for use by itself as a diaper (i.e., without the use of a separate plastic, or other backing sheet), the adhesive must bond the fibers together in the lower surface of the web to provide a structurally stable back surface 84. Though preferred, it is not required to provide bonded networks 86 completely through the web. Therefore, it is within the scope of this invention to maintain the entire interior portion of the fibrous web free of adhesive. Also, it is within the scope of this invention to flow an excessive amount of adhesive onto the upper surface of the fibrous web from a weir box, and remove excess adhesive by pulling it through the web by the application of a vacuum from the underside of the web. In this manner the fibrous web, at least in the flanking end and side portions, will be completely bonded by adhesive through the thickness thereof. In view of the high basis weight in the medial portion 66 of the diaper, it is doubtful whether complete adhesive penetration through said medial portion will be achieved.

Figure 5:
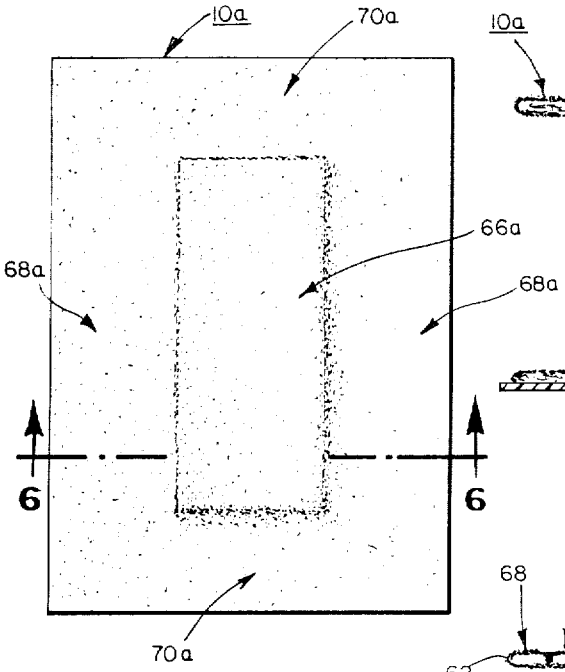
FIG. 5 is a plan view of an absorbent article according to this invention.
Figure 6:
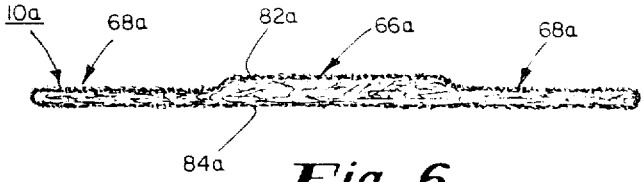
FIG. 6 is a sectional view along line 6—6 of FIG. 5.

Referring to FIGS. 5 and 6, a second embodiment of a unitary, absorbent article 10a, in the form of a disposable diaper, includes flanking side portions 68a, flanking end portions 70a and a medial portion 66a. These portions are the same as the corresponding portions of the diaper described above in connection with FIGS. 9 and 10, with the exception that no embossed pattern is impressed into the web. Referring to FIG. 6, an upper adhesive layer and a lower adhesive layer bond substantially all of the surface fibers together and extend only partially through the thickness of the web to provide an abrasion resistant facing surface 82a and a structurally stable back surface 84a. The interior fibers throughout substantially the entire web are substantially free of adhesive to provide an excellent moisture containing interior region. The diaper disclosed in FIGS. 5 and 6 can be made according to the process of FIG. 1 by replacing the embossing rolls 36 and 38 with plain-surfaced compaction rolls. The use of compaction rolls is desired to slightly compress the web to impart sufficient structural integrity to said web so that it can be conveyed through the subsequent treatment operations.

Figure 7:
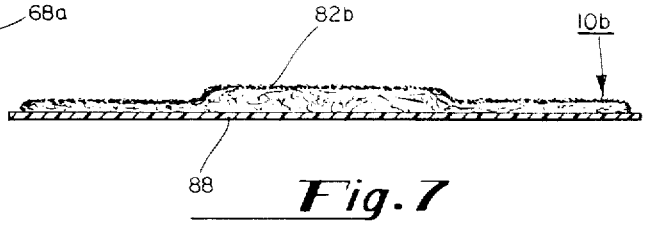
FIG. 7 is a sectional view similar to FIG. 6, but showing an alterative embodiment of this invention.

Referring to FIG. 7 a third embodiment of a disposable diaper 106 is shown. This diaper includes a fluid imperious plastic sheet 88 adhered to the lower surface of the fibrous web. The fibrous web has an upper adhesive layer bonding substantially all of the upper surface fibers together to provide an abrasion resistant, non-pilling facing layer 82b. In this embodiment, a lower adhesive layer can be omitted, and the plastic sheet 88 can be extruded in a plastic state directly onto the fibrous web. Alternatively, a lower layer of adhesive can be applied to the web, and while in a tacky state, it can be utilized to adhere the plastic sheet 88 to the web. The adhesive can be applied continuously over the lower surface of the web, or along spaced lines, dots, or any other desired pattern which will adhere the plastic sheet 88 to the web. Alternatively, the adhesive can be applied either continuously or discontinuously directly to the plastic sheet 88.

Figure 8:
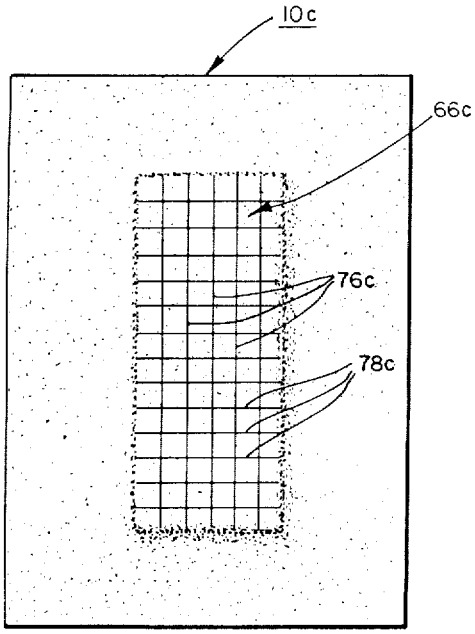
FIGS. 8 and 9 are plan views showing two other alternative embodiments of this invention.

Referring to FIG. 8, a further embodiment of a unitary, absorbent article 10c, in the form of a disposable diaper, is identical to the absorbent article 10a shown in FIG. 5, except that an embossed pattern is impressed only into a medial portion 66c thereof. This embossed pattern is identical to the embossed pattern impressed into the medial portion 66 of the article 10 shown in FIG. 9, and includes transversely spaced longitudinal channels 76c and longitudinally spaced transverse channels 78c.

Figure 11:
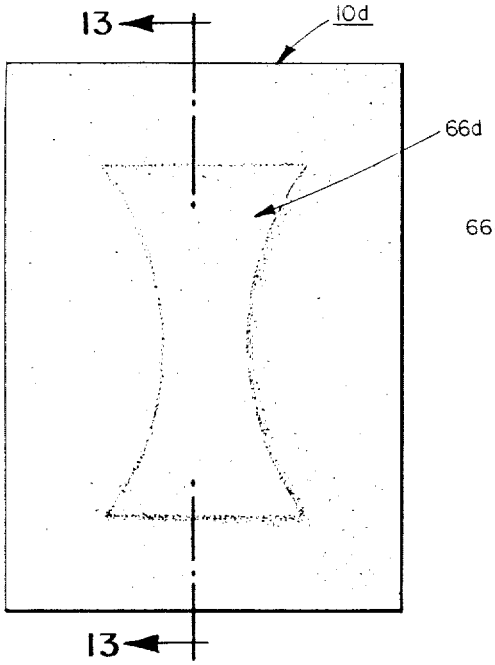
FIGS. 11 and 12 are plan views of two further embodiments according to this invention.
Figure 13:
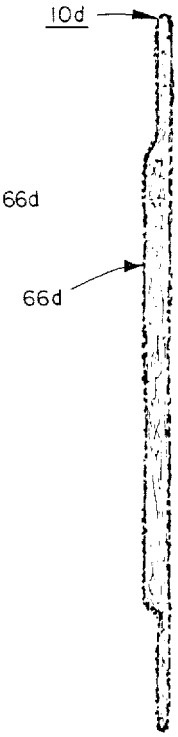
FIGS. 13 and 14 are enlarged sectional views along lines 13—13 and 14—14 of FIGS. 11 and 12, respectively.

FIGS. 11 and 13 disclose an additional embodiment of an absorbent article 10d according to this invention. The absorbent article 10d is identical to the absorbent article 10a shown in FIG. 5 except that a medial portion 66d thereof has a substantially hourglass-shaped configuration providing a reduced width central crotch reguion to provide a construction which conforms confortably to the perineal region of a wearer.

Figure 12:
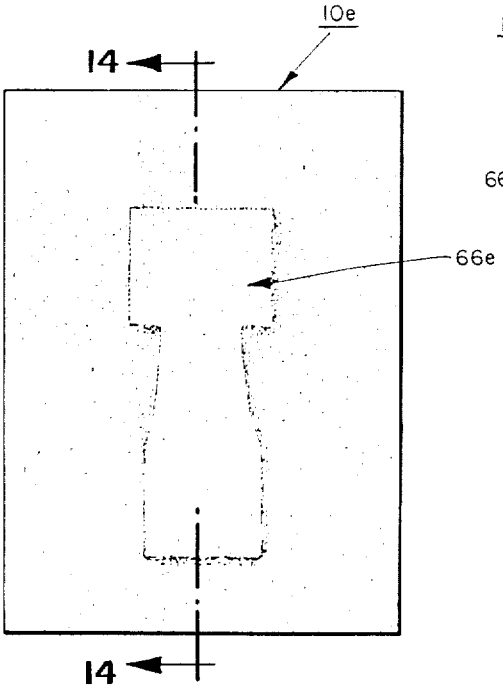
Figure 14:
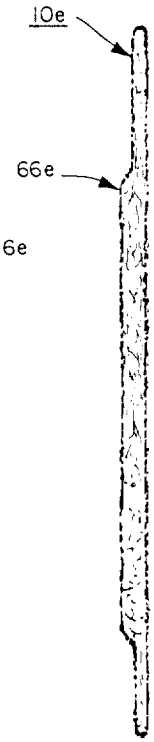

Referring to FIGS. 12 and 14, an additional embodiment of an absorbent article 10e according to this invention is identical to the absorbent article 10a (FIG. 5) and 10d (FIG. 11), except that a medial portion 66e has a different shape. The medial portion 66e has a reduced width central crotch region to provide a construction which conforms comfortably to the perineal region of a wearer.

Figure 15:
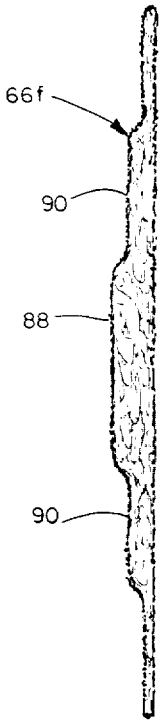
FIGS. 15 and 16 are enlarged sectional views similar to FIGS. 13 and 14, respectively, but showing further embodiments of this invention.
Figure 16:
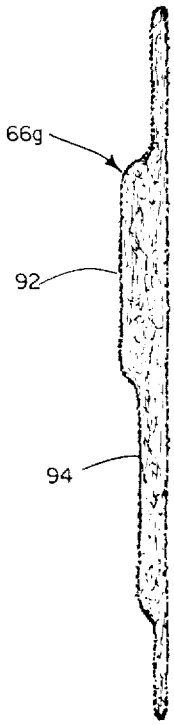

The above-described absorbent articles all include a medial portion having a substantially uniform basis weight throughout its entire extent. However, for some applications, it is desired to provide a profiled medial portion, i.e., a medial portion having different basis weights in different predetermined sections thereof. For example, referring to FIG. 15, when an absorbent article is intended for use as a disposable diaper for a girl, it is desirable to provide a center section 88 of a medial portion 66f with a greater basis weight of fibers therein than adjoining end sections 90 of said medial portion. This construction is preferred because girl babies tend to directly impinge urine into the medial regions of the diaper. Alternatively, referring to FIG. 16, when an absorbent article is intended for use as a disposable diaper for a boy baby, it is desirable to provide a forward section 92 of a medial portion 66g with a greater basis weight of fibers therein than a rearward section 94 of said medial portion. This is preferred because boy babies tend to directly impinge urine onto the forward one-half of the medial portion of the diaper. Preferably the greatest basis weight section in the fibrous webs shown in FIGS. 15 and 16 is between about 17 oz/yd$^2$ and about 50 oz/yd$^2$; and the sections of lesser basis weight are between about 8 oz/yd$^2$ and 22 oz/yd$^2$.

The embodiments shown in FIGS. 7, 11, 12, 15 and 16, can all be provided with embossed patterns in the same manner as described above in connection with the fibrous webs 10 (FIG. 9) and 10c (FIG. 8). The specific patterns which are embossed into the fibrous webs can be varied, and are not intended to be limiting on the present invention. In addition, all of the fibrous webs can be employed by themselves as a unitary cloth-like diaper, or in conjunction with a fluid-impervious plastic sheet, such as is shown in FIG. 7.

It is critical to all embodiments of this invention that the absorbent articles include a high basis weight medial portion and lower basis weight flanking side portions and end portions. The high basis weight medial portion provides a high fluid absorbing area which is positioned in the perineal region of a wearer. In addition, this medial portion provides a relatively conformable construction since it does not extend the full transverse extent of the fibrous web. The most conformable construction results from providing a reduced width crotch region in the manner shown in FIGS. 11 and 13. The low basis weight flanking side portions provide an extremely conformable construction for snugly engaging the thigh regions of a wearer. The low basis weight flanking end portions provide a conformable waist band region for closely encircling the front and back regions of a wearer.

Figure 2:
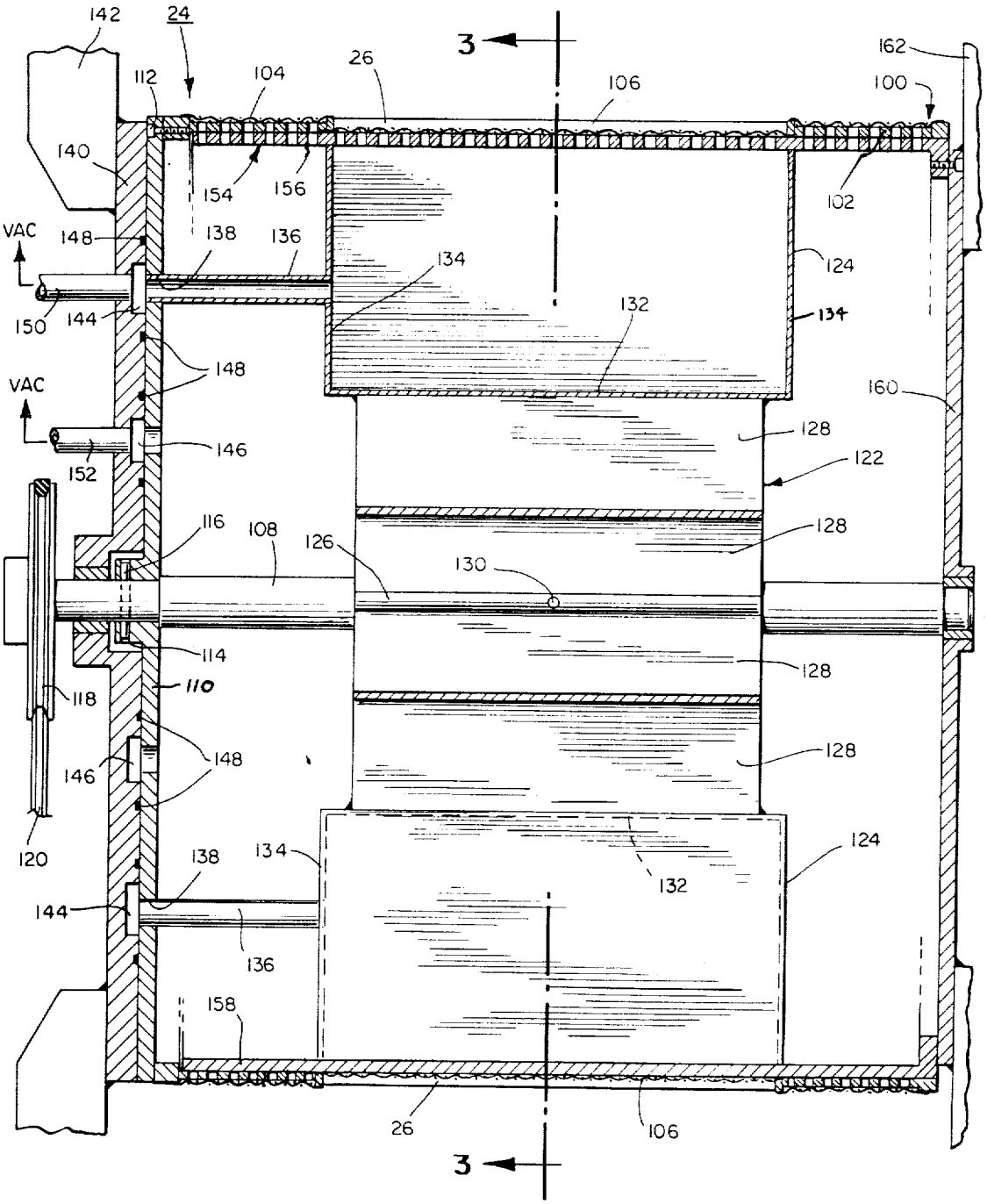
FIG. 2 is a cross-machine-direction sectional view through the condenser roll assembly of this invention taken along line 2—2 of FIG. 3.
Figure 3:
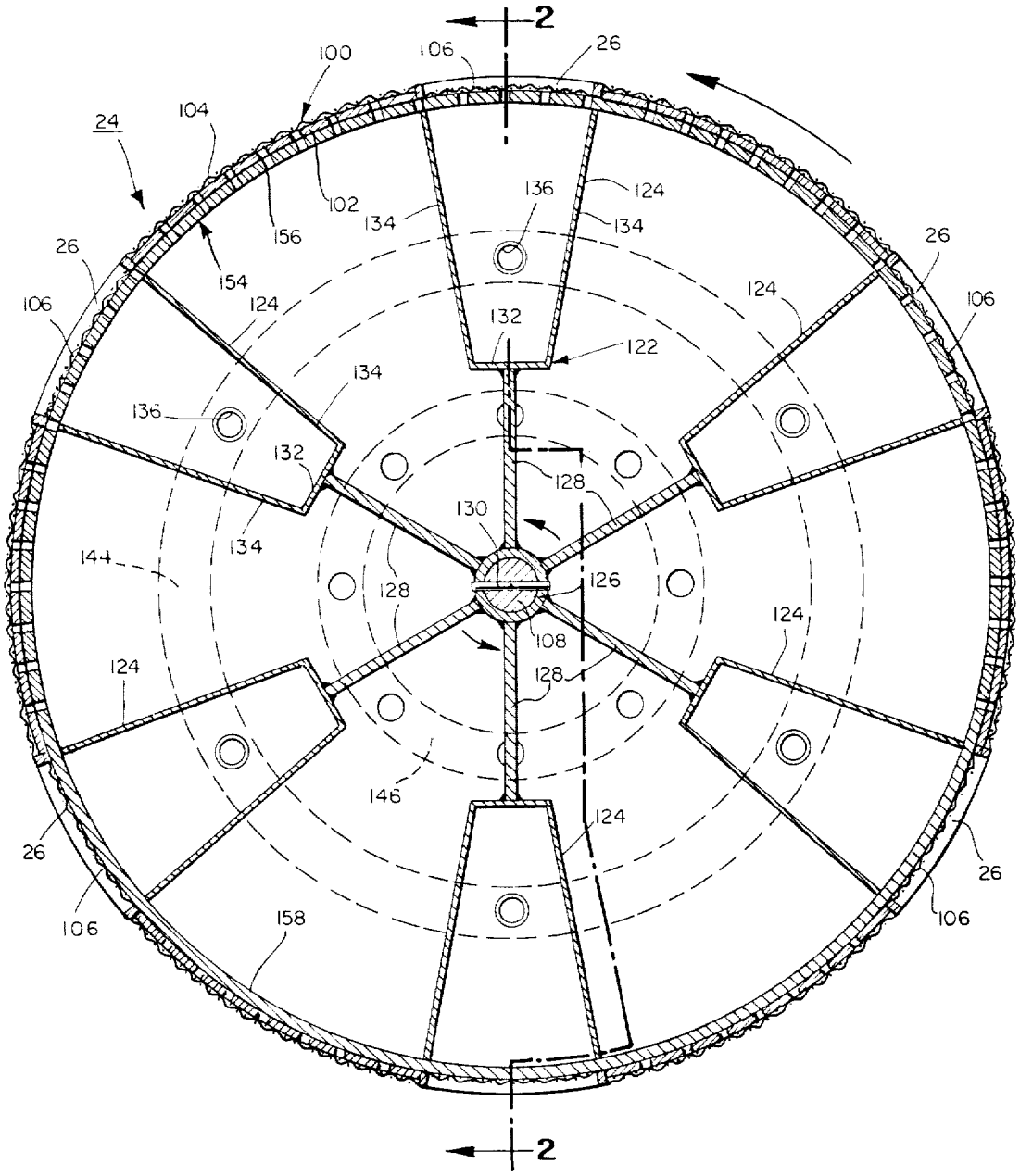
FIG. 3 is a sectional view along line 3—3 of FIG. 2.

Referring to FIGS. 2 and 3, a unique condenser roll assembly 24 of this invention which is employed in the web forming device 14 for forming the continuous fibrous web 16 with spaced, uniform basis weight thickened regions 30 therein will now be described. The condenser roll assembly 24 includes an air-previous condenser roll 100 including a perforated, cylindrical metal shell 102, and a porous screen 104 secured about the outer periphery of said shell. The spaced, three-dimensional compartments 26 are established by providing circumferentially spaced, discrete cut out regions in the porous screen and cylindrical metal shell, and securing a foraminous member 106 to the lower surface of the metal shell 102 to bridge each cut out region and form the bottom wall of the three-dimensional compartments 26. The porous screen 104 and the foraminous member 106 provide the forming surface 22 (FIG. 1) of the condenser roll 100.

The condenser roll 100 is attached to a driven axle 108 through a connecting plate 110. The connecting plate 110 is connected to the cylindrical metal shell 102 of the condenser roll 100 by any suitable fastening means, such as screws 112 (only one of which is shown in FIG. 2). The connecting plate 110 includes a central, hollow hub 114 which is keyed to the driven axle 108 through a connecting pin 116. A pulley 118 is fixedly secured to the axle 108, and a belt 120 is in driving engagement with said pulley for rotating said axle, to thereby rotate the condenser roll 100. The belt 120 is driven by any suitable power source, such as an electric motor (not shown).

A vacuum box assembly 122 is mounted within the condenser roll 100, and is secured to driven axle 108 to be rotated at the same angular velocity as said condenser roll. The vacuum box assembly 122 includes a plurality of vacuum boxes 124 attached to a hollow, cylindrical hub 126 through spoke-like support arms 128. The driven axle 108 extends through the cylindrical hub 126 and is keyed to said hub through a connecting pin 130. Each vacuum box 124 includes a bottom wall 132 and peripheral side walls 134. The outer edges of the peripheral side walls 134 define an opening into each vacuum box 124 having substantially the same shape as the three-dimensional compartments 26, and each vacuum box 124 is aligned with a respective three-dimensional compartment. Since the condenser roll 100 and vacuum box assembly 122 are rotated at the same angular velocity, each vacuum box 124 will underlie its respective compartment 26 throughout the entire path of travel of the condenser roll assembly 24. A vacuum connection conduit 136 is in communication with each vacuum box 124 through a peripheral side wall 134 thereof, and each of said vacuum connection conduits 136 is mounted in communication with a corresponding opening 138 in the connecting plate 110.

Referring to FIG. 2, an end plate 140 is positioned in sliding engagement with the outer surface of the connecting plate 110 and is mounted to fixed structural framework schematically shown at 142. The end plate 140 includes an outer annular recess 144 and an inner annular recess 146 in the inner surface thereof, and these recesses ae concentric to the hub 114 of the connecting plate 110. Suitable elastomeric seals 148 are provided about each of the annular recesses 144 and 146. Suitable sources of vacuum, such as fans (not shown) are connected through vacuum lines 150 and 152 which are in communication with the annular recesses 144 and 146, respectively. In this manner, the vacuum source which is in communication with the outer annular recess 144 will be effective to establish a pressure drop across the bottom foraminous wall 106 of the three-dimensional compartments 26 through the underlying vacuum boxes 124. The other vacuum source, which is in communication with the inner annular recess 146, will be effective to establish a pressure drop across the remaining regions of the foraminous forming surface 22 (FIG. 1).

In order to permit easy removal of the formed web 16 from the condenser roll 100, it is desirable to terminate the partial vacuum through the foraminous forming surface 22 at the point of removal. To achieve this result a masking member 154 is positioned between the condenser roll 100 and the vacuum box assembly 122. The masking member 154 includes a perforated cylindrical shell 156 constructed of any suitable bearing material, said shell having an unperforated lower region 158. Accordingly, as a region of the condenser roll 100 passes over the unperforated region 158 of the cylinder 156, the partial vacuum which is established through vacuum lines 150 and 152 (FIG. 2) will not be effective to establish a partial vacuum through the forming surface 22 to retain allegiance of the formed continuous fibrous web 16 for the condenser roll 100. Therefore, the formed web 16 can be easily transferred to a conveyor (not shown) positioned adjacent the lower side of the condenser roll 100 by applying a partial vacuum through said conveyor. The cylinder 156 is nonrotatably mounted within the condenser roll 100 by being secured to an end support 160 which in turn is attached to fixed structural framework schematically indicated at 162 (FIG. 2).

In practicing the method of this invention a greater partial vacuum is established through the vacuum line 150, which is in communication with the vacuum boxes 124, than is established through the vacuum line 152 which is in communication with the remaining interior portion of the condenser roll 100. Since the entire forming surface 22 of the condenser roll 100 is exposed to vacuum for the same period of time, a greater effective or total volumetric air flow will be established through the bottom walls of the three-dimensional compartments 26, than is established through the surfaces flanking said three-dimensional compartments. This greater effective volumetric air flow results in the deposition of a greater weight of fibers in each of the three-dimensional compartments 26 than on the foraminous surface regions flanking said three-dimensional compartments to thereby establish formation of the continuous fibrous web 16 with spaced, thickened regions 30. The thickened regions 30 of the continuous fibrous web 16 can be formed with any desired shape by providing the three-dimensional compartments 26 and the outer periphery of the vacuum boxes with such desired shape.

The above-described method is effective for forming a thickened medial region which has a substantially uniform basis weight throughout substantially its entire extent. However, in some instances, it is desired to provide a thickened medial region having different basis weights in different predetermined sections thereof, as described above in connection with FIGS. 15 and 16.

Figure 17:
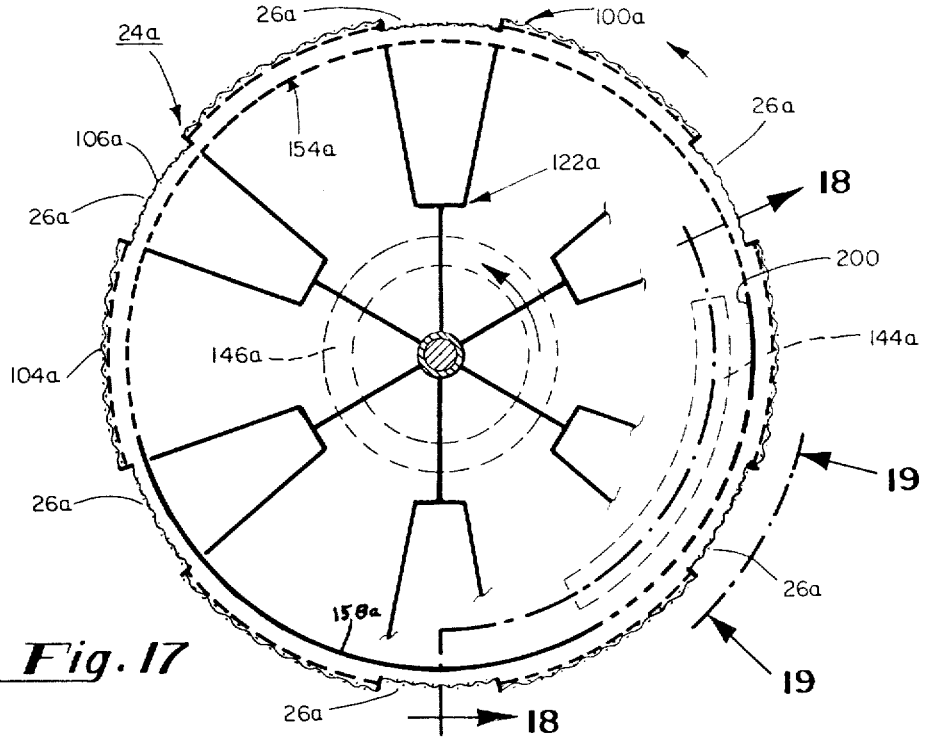
FIG. 17 is a schematic sectional view, similar to FIG. 3 but showing an alternative condenser roll assembly according to this invention.
Figure 18:
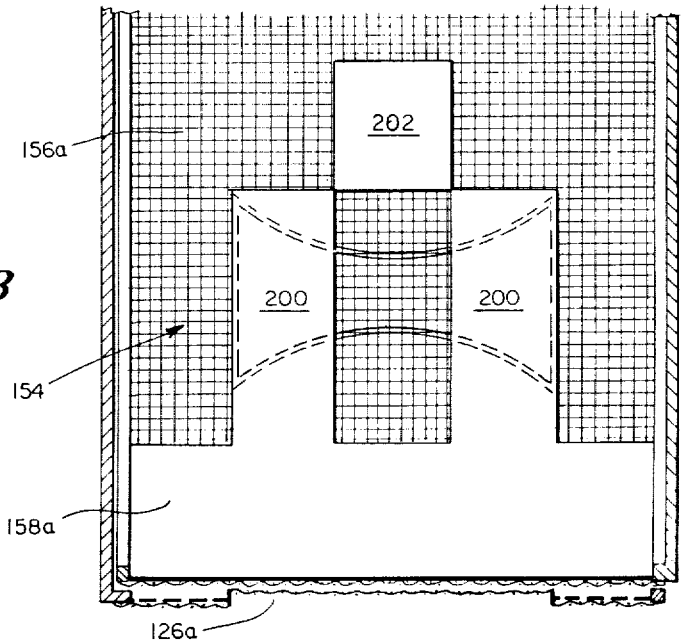
FIG. 18 is a sectional view along line 18—18 of FIG. 17.
Figure 19:
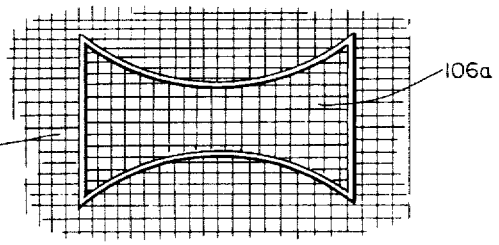
FIG. 19 is a plan view along line 19—19 of FIG. 17.

Referring to FIGS. 17 through 19, a condenser roll assembly 24a is shown which is utilized for forming profiled, thickened medial regions having different basis weights in different predetermined sections thereof. Specifically, the description which follows will be directed to a condenser roll assembly 24a employed in forming hourglass-shaped, thickened medial regions, as shown in FIG. 11, having a greater basis weight in the center crotch section thereof than in flanking end sections thereof, as shown in FIG. 15.

Referring to FIG. 17, the condenser roll assembly 24a includes a condenser roll 100a, a vacuum box assembly 122a, and a masking member 154a which are assembled in the identical manner described earlier in connection with FIGS. 2 and 3. The condenser roll assembly 24a differs from the condenser roll assembly 24 shown in FIG. 2 in the specific construction of the masking member 154a and the specific construction of the end plate (not shown in detail) which are employed.

Referring to FIGS. 17 and 18, the masking member 154a has a lower circumferential extent thereof 158a which is unperforated, and therefore air-impervious, to permit removal of a formed fibrous web from the condenser roll 100a in the same manner described above in connection with the condenser roll assembly 24. In addition, the masking member 154a has axially spaced, circumferentially extending, air-impervious regions 200 which are axially aligned with end sections of three-dimensional compartments 26a as said three-dimensional compartments pass thereover; and a centrally disposed, circumferentially extending, air-impervious region 202 which is axially aligned with the center section of the three-dimensional compartments 26a as said compartments pass thereover (FIG. 18). The circumferential extent of the end air-impervious regions 200 is greater than the circumferential extent of the central air-impervious region 202 for a reason to be described later in this application. The specific orientation of the masking member 154a relative to the condenser roll 100a will depend upon the specific location of the web forming area; therefore, the orientation of the masking member 154a shown in FIG. 17 should not be considered as representing the specific relationship required during use of the condenser roll assembly 24a.

The end plate (not shown in detail) is mounted in engagement with a connecting plate (not shown), which is identical to connecting plate 110, in the same manner as described earlier for connecting the end plate 140 to the connecting plate 110 (FIG. 2). The end plate includes an outer annular recess 144a (FIG. 17) for establishing a vacuum communication between a vacuum source (not shown) and the vacuum boxes 124a. This annular recess extends for substantially the same circumferential extent, and in circumferential alignment with, the end and central air-impervious regions 200 and 202 of the masking member 154a. In this manner, a vacuum will be established through the vacuum boxes 124a only when the three-dimensional compartments 26a, and the corresponding vacuum boxes 124a, are moving within the circumferential region which includes the end mask regions 200 and the central mask region 202 of the masking member 154a to thereby provide substantially complete formation of the hourglass-shaped medial portion 66f (FIG. 15) of the fibrous web in this circumferential region. To further explain, after each three-dimensional compartment 26a completely passes the central mask region 202, the vacuum conduit associated with its corresponding vacuum box will be out of alignment with the outer recess 144a, and therefore, the vacuum established through the vacuum conduit will not be effective to establish a partial vacuum through said vacuum box.

The inner annular recess 146a in the end plate is identical to the inner annular recess 146 described above in connection with FIGS. 2 and 3. This inner annular recess 146a is in communication with the interior of the condenser roll 100a in the regions surrounding the vacuum box assembly 122a. Therefore, the sections of the fibrous web which circumscribe the thick, hourglass-shaped medial portion 66f thereof can be formed throughout the entire circumferential path of travel of the condenser roll assembly 24a through the forming area of the web forming device, and this circumferential extent is greater than the circumferential extent which is circumscribed by the end mask regions 200 and central mask region 202. The vacuum level established through the inner annular recess 146a is set to achieve only sufficient air flow to deposit the desired basis weight of fibers in the portions of the fibrous web circumscribing the hourglass-shaped thickened medial portion 66f.

Since the end masking regions 200 have a greater circumferential extent that the central mask region 202, the center section of the hourglass-shaped compartments of the condenser roll will be exposed to the same vacuum, level as the end sections of said compartments, but for a greater length of time. Accordingly, a greater volumetric air flow is established through the center section of the three-dimensional compartments 26a than through the end sections to achieve formation of the hourglass-shaped thickened medial region 66f having the profile shown in FIG. 15.

A fibrous web having a thickened medial portion as indicated at 66g in FIG. 16 can be formed by employing a condenser roll assembly similar to that shown in FIG. 17. However, the shape of the three-dimensional compartments will be suitable modified to correspond to the shape of the thickened medial portion 66g. In addition, the air-impervious regions of the mask will be positioned to expose one-half of the three-dimensional compartments to vacuum for a greater length of time than the other half to thereby establish the formation of a profiled thickened medial region having a greater basis weight in one-half thereof than in the other half thereof as is shown in FIG. 16.

Other profiles can be established by suitably modifying the masking member. In addition, fibrous webs having different shaped thickened medial regions can be formed by changing the shape of the three-dimensional compartments and the shape of the vacuum boxes. Furthermore, it is within the scope of this invention to provide a fluid impervious coating directly on the forming surface of the condenser roll in the form of a transverse stripe disposed intermediate adjacent three-dimensional compartments to achieve direct formation of discrete fibrous webs on the forming surface.

Having described my invention, I claim:

1. An absorbent article suitable for use as a disposable diaper and the like; said absorbent article comprising a unitary assemblage of randomly arranged fibers in the form of a web, said web having a transverse dimension defined between spaced, elongate side edges and an elongate dimension defined between spaced end edges; a medial portion of said web having a greater basis weight and greater average thickness than flanking end and side portions thereof for establishing a step configuration in a upper surface of said web in both the elongate and transverse direction; adhesive means on said upper surface of said web for bonding together exposed surface fibers in said upper surface to provide an abrasion resistant, non-piling, facing layer, and to aid in maintaining the structural integrity of said web and stabilizing means for stabilizing a lower surface of said web; said upper surface being adapted to be positioned in contact with a wearer with the medial portion of the web in the perineal region, the flanking side portions about the thigh regions, and the flanking end portions about the front and back regions.

2. The absorbent article according to claim 1, wherein said flanking end and side portions have substantially the same basis weight and thickness.

3. The absorbent article according to claim 2, wherein said stabilizing means is adhesive on said lower surface for bonding together exposed surface fibers in said lower surface.

4. The absorbent article according to claim 2, wherein said stabilizing means includes a moisture-impervious sheet secured to said lower surface.

5. The absorbent article according to claim 2, wherein said randomly arranged fibers include a major proportion by weight of short cellulosic fibers of a papermaking length of less than 1/4 inch, and a minor proportion by weight of reinforcing fibers having an average length over 1/4 inch interspersed and randomly intermingled with said short cellulosic fibers to enhance the strength of said web.

6. The absorbent article according to claim 2, wherein said medial portion includes sections of different basis weights, the greatest basis weight being a section where it is most needed to absorb body fluids.

7. The absorbent article according to claim 2, wherein said adhesive means only partially penetrates through the thickness of said web in the medial portion thereof to leave interior fibers of said medial portion unbonded by adhesive.

8. The absorbent article according to claim 7, including compressed regions in the upper surface of the medial portion of the web to enhance wicking of fluids along said medial region.

9. The absorbent article according to claim 8, further including compressed regions in said flanking side and end portions disposed in a predetermined pattern and separated by substantially uncompressed high loft regions.

10. The absorbent article according to claim 9, wherein said adhesive means defines bonded networks completely through the web in only the compressed regions of the flanking end and flanking side portions thereof.

11. The absorbent article according to claim 2, wherein said medial portion joins said flanking side portions along side boundaries and joins said end portions along end boundaries, at least a portion of said side boundaries being recessed to define a narrow center crotch section adapted to be positioned in the perineal region of a wearer, said medial portion further including a forward section and rearward section disposed, respectively, on opposite sides of the crotch section, said forward and rearward sections having a greater transverse dimension than said crotch section.

12. The absorbent article according to claim 11, wherein said medial portion includes sections of different basis weights, the greatest basis weight being in a section where it is most needed to absorb body fluids.

*13. A multi-layer disposable diaper comprising*

*(1) a highly porous batt comprised at least primarily of short cellulosic fibers and*

*(2) a water-impervious backing sheet adjacent one surface of said batt and bonded thereto in spaced areas of adhesion, the fibers of said batt being bonded together by a resinous binder covering the surface opposite said backing sheet to provide a smooth permable skin as a body contacting surface of said batt, said resinous binder extending throughout the thickness of said batt in spaced linear areas.*

*14. The diaper of claim 13, wherein said backing sheet is adhered to said batt by a separate adhesive in the marginal areas of the region of contact between said backing sheet and said batt.*

*15. The diaper of claim 13, wherein said binder contains a surfactant.*

*16. The diaper of claim 13, wherein said binder is a thermoset material.*

*17. The diaper of claim 13, wherein said highly porous batt is comprised entirely of short fibers.*

*18. The diaper of claim 13, wherein said highly porous batt is comprised of short fibers and long fibers.*

*19. The diaper of claim 18, wherein said short and long fibers are uniformly blended.*

*20. A method of making a diaper comprising the steps of applying a liquid resinous binder to a surface of highly porous batt of short cellulosic fibers, compressing said batt in spaced linear areas to cause said liquid resinous binder to move through the thickness of said batt in said area, solidifying said binder to provide a smooth liquid permable skin as a body contacting surface of said batt and to form spaced binder walls extending throughout the thickness of the batt and adhering the surface of said batt opposite said first named surface to a water-impervious backing sheet.*

*21. The method of claim 20, wherein said liquid resinous binder is an aqueous latex of a thermosetting material.*

*22. The method of claim 20, wherein said liquid resinous binder contains a surfactant.*

* * * * *